United States Patent [19]

Kakimoto

[11] Patent Number: 4,579,961
[45] Date of Patent: Apr. 1, 1986

[54] ORGANOGERMANIUM COMPOUNDS HAVING BOTH HYDROPHILICITY AND LIPOPHILICITY AND PROCESS FOR PRODUCING THE SAME

[76] Inventor: Norihiro Kakimoto, 3599-23, Honmachida, Machidashi, Tokyo, Japan

[21] Appl. No.: 578,959

[22] Filed: Feb. 10, 1984

[51] Int. Cl.[4] .............................................. C07F 7/30
[52] U.S. Cl. ...................................... 556/83; 514/492
[58] Field of Search ...................... 260/429 R; 556/83

[56] References Cited

U.S. PATENT DOCUMENTS

| 3,689,516 | 9/1972 | Asai et al. | 260/429 R |
| 3,812,167 | 5/1974 | Pahk | 260/429 R |
| 4,066,678 | 1/1978 | Sato et al. | 260/429 R |
| 4,271,084 | 6/1981 | Ishikawa et al. | 260/429 R |
| 4,420,430 | 12/1983 | Chang et al. | 260/429 R |

FOREIGN PATENT DOCUMENTS

| 0086569 | 8/1983 | European Pat. Off. | 260/429 R |
| 3215417 | 10/1983 | Fed. Rep. of Germany | 260/429 R |
| 0160319 | 12/1979 | Japan | 260/429 R |

Primary Examiner—Helen M. S. Sneed
Attorney, Agent, or Firm—Burns, Doane, Swecker & Mathis

[57] ABSTRACT

Organogermanium compounds having both hydrophilicity and lipophilicity are respresented by the formula

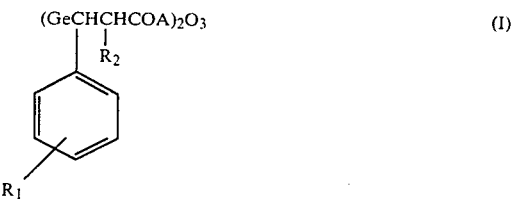

in which $R_1$ and $R_2$ are each a hydrogen atom or a lower alkyl group, and A is a hydroxyl or amino group, a salt thereof, or an O-lower alkyl group. The compounds are produced by a process which comprises obtaining a trihalogermylcinnamic acid derivative of the formula

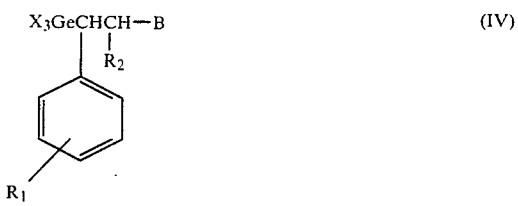

in which $R_1$ and $R_2$ are each a hydrogen atom or a lower alkyl group, and B is a cyano, carboxyl, haloformyl, or carbamoyl group, or a group esterified with a lower alkyl group, directly or indirectly from a cinnamic acid derivative of the formula

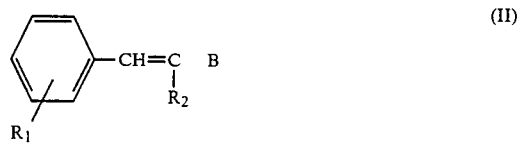

in which $R_1$, $R_2$, and B are as defined above, and a trihalogermane

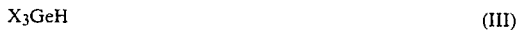

and then hydrolyzing the derivative (IV).

1 Claim, No Drawings

ORGANOGERMANIUM COMPOUNDS HAVING BOTH HYDROPHILICITY AND LIPOPHILICITY AND PROCESS FOR PRODUCING THE SAME

BACKGROUND OF THE INVENTION

This invention relates to organogermanium compounds having both hydrophilicity and lipophilicity and a process for producing them.

There have been known a number of alkyl- and arylgermanium sesquioxides obtained as hydrolyzates of trialkyl- and triarylgermanes. Of these hydrolyzates, carboxyethylgermanium sesquioxide is drawing attention as an immunotherapeutic agent completely free from toxicity.

Many of the known alkyl- and arylgermanium sesquioxides dissolve little in water and organic solvents. Only the carboxyethylgermanium sesquioxide and some of its derivatives have solubilities of 1 to 2% in water, or only slight hydrophilicity. No lipophilic oxide has ever been available. Thus, without affinity for the lipids that are essential constituents of the living organism, such a prior art compound is retained only for a very short period in the body on account of the metabolism of limited duration. In order that it be efficacious, therefore, its dosage must be relatively increased to disadvantage.

Metallic germanium, the chief material of the germanium compounds, is expensive itself and its annual production is limited. Relative decrease rather than increase in the dosages is an important problem to be solved for conservation of germanium resources as well as from the economical viewpoint.

In view of the foregoing, we have intensively conducted experiments aimed at providing an organogermanium compound which is free of toxicity and achieve the dual purpose of being rapidly absorbed by the patient and excreted from the body while exhibiting and maintaining an effective pharmacological activity per given dose. The present invention has now been perfected after syntheses of numerous compounds.

SUMMARY OF THE INVENTION

In accordance with the invention, organogermanium compounds are provided which are characterized by the general formula

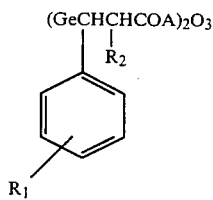

(I)

in which $R_1$ and $R_2$ are each a hydrogen atom or a lower alkyl group, and A is a hydroxyl or amino group, a salt thereof, or an O-lower alkyl group.

Also, a process for producing the organogermanium compounds is provided which is characterized by the steps of obtaining a trihalogermylcinnamic acid derivative of the formula

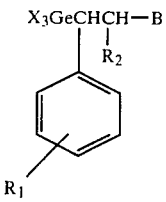

(IV)

where $R_1$ and $R_2$ are each a hydrogen atom or a lower alkyl groups, and B is a cyano, carboxyl, haloformyl, or carbamoyl group or a groups esterified with a lower alkyl group, directly of indirectly from a cinnamic acid derivative of the formula

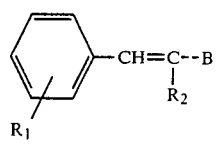

(II)

where $R_1$, $R_2$, and B are as defined above, and a trihalogermane $$X_3GeH \quad (III)$$

and then hydrolyzing the trihalogermylcinnamic acid derivative.

DETAILED DESCRIPTION OF THE PREFERRED EMBODIMENTS

The compounds of the present invention, as is obvious from the formula (I), are alkylgermanium sesquioxides, in which a phenyl group having a substituent $R_1$ is bonded to the $\alpha$-position of the germanium atom and a substituent $R_2$ is bonded to the $\beta$-position, and a substituent X is bonded to the carbonyl group. Substituents $R_1$ and $R_2$ are each a hydrogen atom or a lower alkyl group such as a methyl, ethyl, or propyl group. The substituent X is a hydroxyl or amino group, a salt thereof such as sodium salt or hydrochloride, or an O-lower alkyl group such as a methoxy or ethoxy group.

Examples of the compounds according to the invention will be given below for illustration.

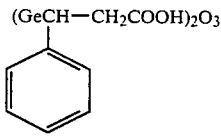

(1)

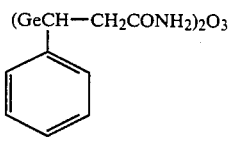

(2)

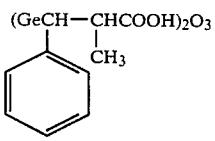

(3)

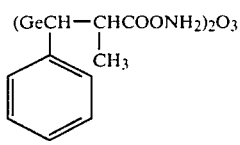

(4)

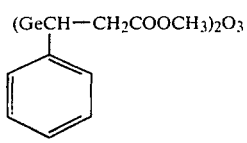

(5)

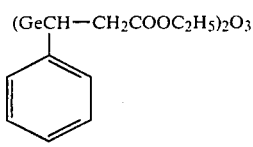

(6)

The compounds of the invention, characterized as described above, are produced generally by preparing a trihalogermylcinnamic acid derivative represented by the formula (IV) directly or indirectly from a cinnamic acid derivative of the formula (II) and a trihalogermane (III), and then hydrolyzing the derivative (IV) to the objective compound. There are two methods for practicing the process of the invention.

In one method an oxygen functional group, for example, a carboxyl group, of the compound (I) according to the invention is introduced beforehand into the cinnamic acid derivative in the following manner:

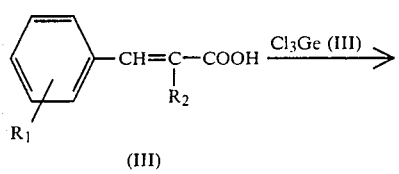

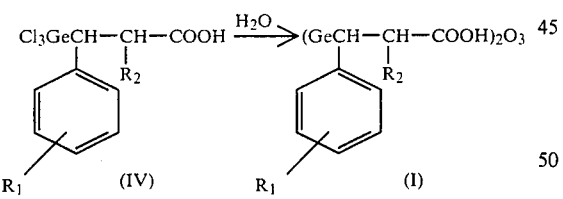

It is alternatively possible to convert the carboxyl group temporarily to a corresponding haloformyl group and reconvert the latter into the carboxyl group on hydrolysis.

The second method involves synthesis of oxygen functional groups in a variety of ways.

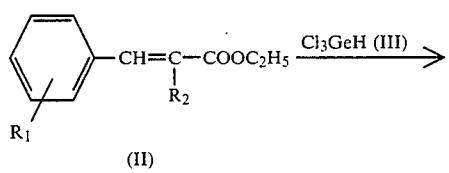

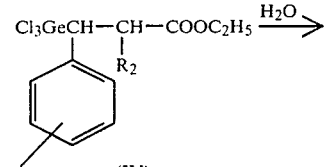

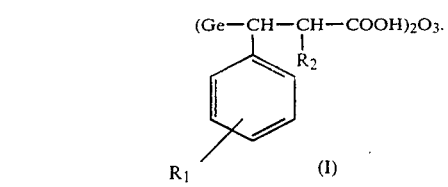

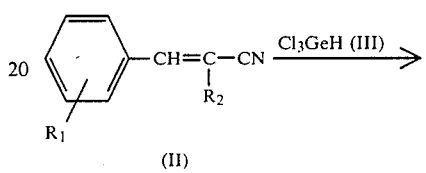

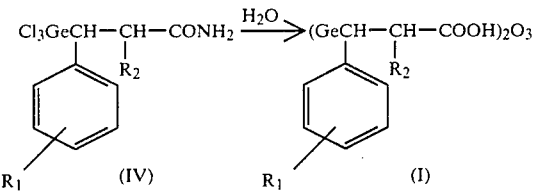

The hydrolysis reaction toward the end of each process formulated above may be carried out using only water or an acid or alkali instead. The reaction sequence is such that the trichlorogermylcinnamic acid derivative (IV) is converted into a corresponding trihydroxygermylcinnamic acid derivative (IV′)

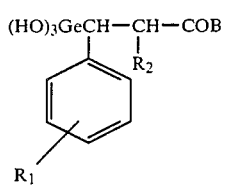

(IV′)

and an intermolecular dehydration-condensation reaction takes place to convert the trihydroxy compound (IV′) to the objective compound (I) of the invention. This means that, like the other alkylgermanium sesquioxides, the compounds of the invention have intermolecular oxygen bridges.

The compounds (I) thus obtained by the process of the invention are hydrophilic, dissolving in water as readily as carboxyethylgermanium sesquioxide and its derivatives. In addition, they are far more lipophilic than known alkyl- or arylgermanium sesquioxides, although the solubilities of the individual compounds in methanol, ethanol, acetone, and ethyl ether vary in the range from about one % to infinity. These compounds (I), when administered to patients, undergo changes in the route and efficiency of absorption and remain for a prolonged time period by virtue of their affinities for the lipids in the body. Consequently, they are expected to achieve improved pharmacological activities and relative decreases in dosages.

EXAMPLE 1

Synthesis of the compound (1) of the invention (1) via β-(trichlorogermyl)hydrocinnamic acid (7)

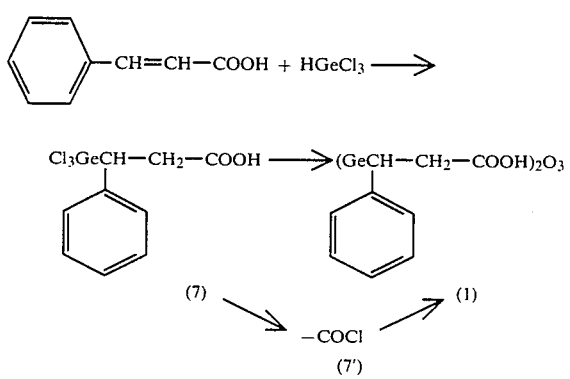

Synthesis of β-(trichlorogermyl)hydrocinnamic acid (7)

After dissolution of 29.6 g (0.2 mol) of cinnamic acid in 100 ml of dry ethyl ether, 36 g (0.2 mol) of trichlorogermane was added. The mixture was stirred for 2 hours, and the ethyl ether was distilled away. The resulting crystalline precipitate was recrystallized from a mixture of benzene and n-hexane in a ratio of 1:5 to give 61.5 g of plates in a yield of 93.8%.

Melting point: 82°–84° C.

Anal. Calcd.: Ge:22.12, C:32.96, H:2.77, Cl:32.41, Found: Ge:22.02, C:32.74, H:2.80, Cl:32.35.

IR(KBr cm$^{-1}$): 3000, 1710, 1420, 1300, 1290, 1250, 700, 420, 400.

Synthesis of the compound (1) of the invention

A solution of 6.56 g (0.02 mol) of the β-(trichlorogermyl)hydrocinnamic acid (7) in 100 ml of water was allowed to stand for 24 hours. The resulting crystals, when recrystallized from hot water, afforded 4.1 g of amorphous crystals. The yield was 83.4%.

Decomposition point: 240° C.

Anal. Calcd.: Ge:29.54, C:43.99, H:3.69 Found: Ge:29.40, C:44.13, H:3.53.

IR(KBr cm$^{-1}$): 3420, 1710, 1495, 1450, 1210–1230, 800–900, 700.

DTA: Exothermic peak at 286° C.

Alternatively, the compound (I) of the present invention may be prepared by synthesizing a chloride (7′) of the β-(trichlorogermyl)hydrocinnamic acid in the following way and then treating the chloride in the manner described above.

Synthesis of β-(trichlorogermyl)hydrocinnamoyl chloride (7′)

Sixty grams of thionyl chloride was added to 16.4 g (0.05 mol) of β-(trichlorogermyl)hydrocinnamic acid (7), and the mixture was heated under reflux for 2 hours. Then excess thionyl chloride was distilled away in the usual manner. The residue, upon vacuum distillation, gave 12.9 g of a fraction, bp 148°–149° C./4 mmHg. The yield was 69.1%.

Colorless oily matter.

Anal. Calcd.: Ge:20.88, C:31.10, H:2.32, Cl:40.80, Found: Ge:20.90, C:29.00, H:2.49, Cl:40.90.

IR(neat cm$^{-1}$): 3000, 1795, 1500, 1455, 1020, 960, 810, 700, 640, 425, 400.

other physical properties: $n_D^{20}$ 1.5736, $d_{20}^{20}$ 1.5793.

(2) via methyl β-(trichlorogermyl)hydrocinnamate (8)

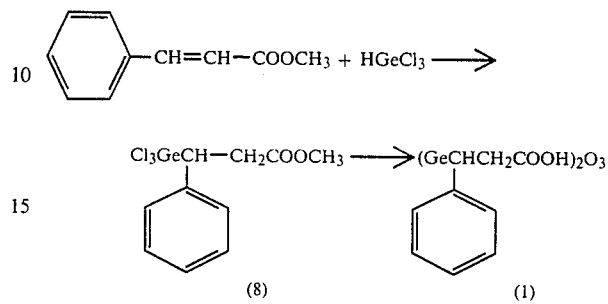

Synthesis of methyl β-(trichlorogermyl)hydrocinnamate (8)

A mixture of 36.0 g (0.2 mol) of trichlorogermane and 32.4 g (0.2 mol) of methyl cinnamate was stirred for 2 hours and then distilled in vacuum to obtain 56.2 g of a fraction, b.p. 148°. Yield 82.2%.

Colorless oily matter.

Anal. Calcd.: Ge:21.22, C:35.11, H:3.24, Cl:31.08, Found: Ge:21.12, C:35.18, H:3.31, Cl:31.15.

IR(neat cm$^{-1}$): 1740, 1450, 1440, 1360, 1220, 765, 700, 420, 400.

other physical properties: $n_D^{20}$ 1.5590, $d_{20}^{20}$ 1.5170.

Synthesis of the compound (1) of the invention

A mixture of 6.8 g of methyl β-(trichlorogermyl)hydrocinnamate and 24 ml of a methanolic solution of sodium carbonate was heated under reflux for one hour, and then the methanol was distilled away. After the addition of 50 ml water, the mixture was made slightly acidic with concentrated hydrochloric acid to allow precipitation of crystals. The crystals upon washing with water and recrystallization from hot water formed 4.0 g of the compound (1) of the invention. Yield 81.2%. This product was exactly the same as that of the invention obtained by procedure (1) above.

EXAMPLE 2

Synthesis of the compound (2) of the invention (1) via β-(trichlorogermyl)hydrocinnamide (9)

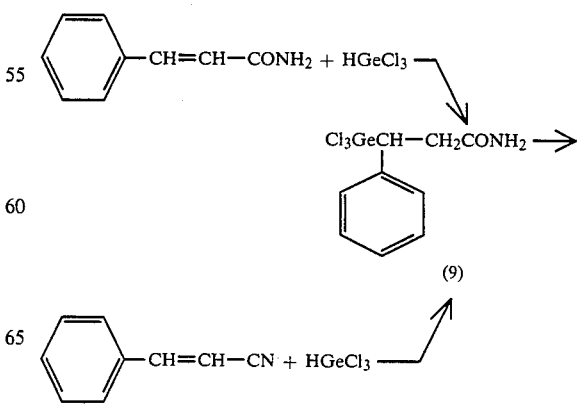

-continued (GeCH—CH$_2$CONH$_2$)$_2$O$_3$
|
C$_6$H$_5$ (2)

Synthesis of β-(trichlorogermyl)hydrocinnamide (9)

To a solution of 29.4 g (0.2 mol) of cinnamamide in 100 ml of dry ethyl ether was added 36 g (0.2 mol) of trichlorogermane. After 2 hours of stirring, the ethyl ether was distilled away from the mixture to effect precipitation of crystals. The precipitate upon recrystallization from chloroform gave 63.5 g of plates. Yield 97.1%.

Alternatively, 500 ml of concentrated hydrochloric acid and 36 g (0.2 mol) of trichlorogermane were added to 25.8 g (0.2 mol) of cinnamonitrile, the mixture was stirred for 6 hours, and the crystalline precipitate was recrystallized from chloroform. In this case the yield was 34.6 g, or 56%.

Melting point: 178°–180° C.

Anal. Calcd.: Ge:22.19, C:33.04, H:3.08, N:4.28, Cl:32.5, Found (based on cinnamamide): Ge:21.88, C:33.12, H:3.15, N:4.34, Cl:32.4, (based on cinnamonitrile): Ge:22.05, C:32.83, H:3.01, N:4.11, Cl:32.59.

IR(KBr cm$^{-1}$): 3450, 3350, 1650, 1580, 1450, 760, 695, 590, 420, 400.

Synthesis of the compound (2) of the invention

One hundred milliliters of concentrated ammonia water was added to 6.5 g (0.02 mol) of β-(trichlorogermyl)hydrocinnamamide. After stirring, the mixture was concentrated to one-third of the original volume, crystals that precipitated were water washed and recrystallized from hot water to obtain 3.1 g of amorphous crystals. Yield 62.0%.

Decomposition point 252° C.

Anal. Calcd.: Ge:29.66, C:44.16, H:4.12, N:5.77, Found: Ge:29.41, C:44.20, H:4.23, N:5.49.

IR(KBr cm$^{-1}$): 3450, 3300, 1660, 1600, 1500, 1450, 1405, 930, 900, 800, 770, 700, 575.

DTA: Exothermic peaks at 307° and 400° C.

(2) via ethyl β-(trichlorogermyl)hydrocinnamate (10)

C$_6$H$_5$—CH=CH—COOC$_2$H$_5$ + HGeCl$_3$ ⟶

Cl$_3$GeCH—CH$_2$COOC$_2$H$_5$ ⟶ (GeCH—CH$_2$COONH$_2$)$_2$O$_3$
|                                                  |
C$_6$H$_5$                                         C$_6$H$_5$

(10)                                              (2)

Synthesis of ethyl β-(trichlorogermyl)hydrocinnamate (10)

A mixture of 36 g (0.2 mol) of trichlorogermane and 35.2 g (0.2 mol) of ethyl cinnamate was stirred for 2 hours, and then the reaction product was distilled under vacuum to afford 56 g of a fraction, b.p. 169°–170° C./4 mmHg. Yield 78.7%.

Colorless oily matter.

Anal. Calcd.: Ge:20.38, C:37.10, H:3.68, Cl:29.86, Found: Ge:20.31, C:36.95, H:3.70, Cl:29.86.

IR(neat cm$^{-1}$): 3000, 1735, 1500, 1460, 1380, 1180–1240, 765, 700, 400–430.

Other physical properties: n$_D^{20}$ 1.5480, d$_{20}^{20}$ 1.4464.

Synthesis of the compound (2) of the invention

In a sealed tube, 7.1 g (0.019 mol) of ethyl β-(trichlorogermyl)hydrocinnamate and 35 ml of concentrated ammonia water were heated at 60° to 80° C. for 24 hours to precipitate crystals. The crystals were filtered, washed with a small amount of water, and recrystallized from hot water. In this way 2.4 g of the compound (2) of the invention was obtained. Yield 49.8%. This product was exactly the same as that of the invention prepared by procedure (1) above.

EXAMPLE 3

Synthesis of the compound (3) of the invention

C$_6$H$_5$—CH=C—COOH + HGeCl$_3$ ⟶
         |
         CH$_3$

Cl$_3$GeCH—CH—COOH ⟶
         |
         CH$_3$
C$_6$H$_5$

(11)
                ↓
              —COCl (11')

(GeCH—CH—COOH)$_2$O$_3$
|      |
C$_6$H$_5$  CH$_3$ (3)

Synthesis of α-methyl-β-(trichlorogermyl)hydrocinnamic acid (11)

To a solution of 32.4 g (0.2 mol) of α-methylcinnamic acid in ethyl ether, 36.0 g (0.2 mol) of trichlorogermane was added. After 2 hours of stirring, the ether was distilled away from the reaction mixture to precipitate crystals. The crystals upon recrystallization from n-hexane gave 50.6 g of plates. Yield 74.2%.

Melting point: 91°–92° C.

Anal. Calcd.: Ge:21.22, C:35.10, H:3.24, Cl:31.09, Found: Ge:21.08, C:35.15, H:3.26, Cl:31.21.

IR(KBr cm$^{-1}$): 3000, 1680, 1465, 1455, 1280–1290, 700, 390–420.

Synthesis of the compound (3) of the invention

A solution of 6.8 g (0.02 mol) of α-methyl-β-(trichlorogermyl)hydrocinnamic acid in 100 ml of water was heated to 60° C. and stirred for 2 hours. Crystals that precipitated were filtered and recrystallized from hot water to afford 4.5 g of amorphous crystals. Yield 86.6%.

Decomposition point: 230° C.

Anal. Calcd.: Ge:27.94, C:46.23, H:4.27, Found: Ge:27.83, C:46.04, H:4.22.

IR(KBr cm$^{-1}$): 3500, 1705, 1455, 840–900, 700.

DTA: Exothermic peak at 264° C.

The compound (3) according to the invention may alternatively be prepared by synthesizing a chloride (11') of the α-methyl-β-(trichlorogermyl)hydrocinnamic acid in the following way and then treating the chloride in the manner described above.

Synthesis of α-methyl-β-(trichlorogermyl)hydrocinnamoyl chloride (11')

A mixture of 300 ml of thionyl chloride and 34.2 g (0.1 mol) of α-methyl-β-(trichlorogermyl)hydrocinnamic acid was heated under reflux. Excess thionyl chloride was distilled away by the usual method and the residue was distilled under vacuum, when 31.5 g of a fraction, b.p. 133°–134° C./3 mmHg was obtained. Yield 92.5%. This fraction crystallized upon standing.

Melting point: 53°–54° C.

Anal. Calcd.: Ge:20.13, C:33.31, H:2.79, Cl:39.33, Found: Ge:20.02, C:33.11, H:2.83, Cl:39.35.

IR (KBr cm$^{-1}$): 3000, 1785, 1455, 940 920, 890, 700, 590, 425, 400.

EXAMPLE 4

Synthesis of the compound (4) of the invention

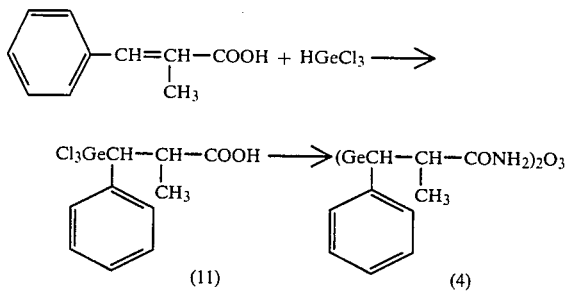

Into 200 ml of concentrated ammonia water 7.2 g (0.02 mol) of the α-methyl-β-(trichlorogermyl)hydrocinnamic acid (11) synthesized as above was dissolved. The solution was heated and evaporated to dryness. Crystals that precipitated were washed with a small amount of water and recrystallized from hot water to afford 3.3 g of amorphous crystals. Yield 64.3%.

Decomposition point: 225° C.

Anal. Calcd.: Ge:28.05, C:46.41, H:4.67, N:5.41, Found: Ge:27.86, C:46.30, H:4.66, N:5.19.

IR(KBr cm$^{-1}$): 3200–3500, 1665, 1495, 1450 1400, 800–900, 700.

DTA: Exothermic peaks at 286° and 317° C.

EXAMPLE 5

Synthesis of the compounds (5), (6) of the invention

The previously synthesized methyl ester (8) or ethyl ester (10) of β-(trichlorogermyl)hydrocinnamic acid was treated with an alcoholic potash in the same manner as in the synthesis of the compound (1) of the invention. The product upon recrystallization from hot water yielded the compound (5) or (6) of the invention.

Compound (5) of the invention

Amorphous crystals.

Decomposition point: 266° C.

IR(KBr cm$^{-1}$): 3000, 1740, 1500, 1460, 1440, 1200–1260, 1170, 800–900, 700.

DTA: Endothermic peaks at 290° and 306° C. and exothermic peak at 328° C.

Compound (6) of the invention

Colorless oily matter

IR(neat cm$^{-1}$): 3000, 1730, 1495, 1455, 1375, 1160–1260, 800–900, 700, 400.

EXAMPLE 6

Solubilities of the compounds of the invention

The compounds (1) through (6) prepared in accordance with the invention were tested for their solubilities in water and various organic solvents. The results are summarized in the following table.

| Compound | Solvent | | | | |
|---|---|---|---|---|---|
| | Water | Methanol | Ethanol | Acetone | Ethyl ether |
| (1) | 0.8~1.1 | 0.6~0.8 | 0.5~0.6 | 0.3~0.35 | 0.03~0.04 |
| (2) | 0.6~0.8 | 0.1~0.2 | — | — | — |
| (3) | 1.0~1.2 | ∞ | ∞ | ∞ | ∞ |
| (4) | 1.0~1.2 | ∞ | ∞ | 0.2~0.25 | — |
| (5) | — | ∞ | ∞ | ∞ | ∞ |
| (6) | — | ∞ | ∞ | ∞ | ∞ |
| | | | | | (W/V %) |

EXAMPLE 7

Pharmacological test of the compound (2) of the invention-(1)

$1 \times 10^6$ IMC carcinomas were implanted hypodermically into female CDF$_1$ mice, 9-week old, in a group of 10 mice (20 mice in a control group) as experimental animal. Starting with the day after the implantation, the compound (2) of the invention was administered perorally for five consecutive days. The weight of the carcinomas was measured on the 21st day after the implantation to determine the inhibition rate.

As shown in the following table, the compound (2) of the invention exhibited an excellent antineoplastic effect.

TABLE

| Compd. administered | Dose (mg/kg/day) | Wt. of carcinoma (g) | Inhibition rate (%) |
|---|---|---|---|
| Control | | 1.59 ± 0.65 | |
| Compound (2) | 25 | 0.96 ± 0.34 | 40 (P < 0.01) |
| " | 5 | 1.12 ± 0.45 | 30 |

EXAMPLE 8

Pharmacological test of the compound (2) of the invention-(2)

Mouse leukemia cells L-1210 were implanted intraperitoneally into female CDF$_1$ mice, 8-week old, in a group of 6 mice as experimental animal, 4 mg/kg of Adriamycin was administered intraperitoneally only once on the next day and the compound (2) of the invention was administered perorally for 10 consecutive days starting with the next day of the implantation. A survival test was carried out for 30 days to examine the effect of the combined use of Adriamycin as a chemotherapeutic agent.

As shown in the following table, an excellent effect of the combined use was observed.

TABLE

| Compd. administered | Amount of compd. (2) (mg/kg/day) | Average survival date (day) | T/C (%) | Survival rate after 30 days |
|---|---|---|---|---|
| Control | | 10.1 ± 0.4 | | 0/6 |
| Adriamycin alone (4 mg/kg) | — | 17.9 ± 3.5 | | 0/6 |
| Adriamycin and compd. (2) | 25 | 24.9 ± 5.1 | 247 ($P < 0.05$) | 3/6 |
| Adriamycin and compd. (2) | 1 | 16.1 ± 2.5 | 159 | 0/6 |

What is claimed is:

1. Organogermanium compounds having both hydrophilicity and lipophilicity, represented by the formula

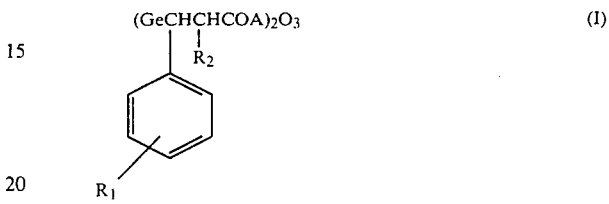

in which $R_1$ and $R_2$ are each a hydrogen atom or a lower alkyl group, and A is a hydroxyl or amino group, a sodium salt or hydrochloride salt thereof, or an O-lower alkyl group.

* * * * *